(12) United States Patent
Furukawa et al.

(10) Patent No.: US 11,298,275 B2
(45) Date of Patent: Apr. 12, 2022

(54) DISPOSABLE DIAPER

(71) Applicant: KAO CORPORATION, Tokyo (JP)

(72) Inventors: Yumi Furukawa, Utsunomiya (JP); Hiromichi Suzuki, Moka (JP)

(73) Assignee: KAO CORPORATION, Tokyo (JP)

( * ) Notice: Subject to any disclaimer, the term of this patent is extended or adjusted under 35 U.S.C. 154(b) by 404 days.

(21) Appl. No.: 16/320,878

(22) PCT Filed: Jul. 25, 2017

(86) PCT No.: PCT/JP2017/026875
§ 371 (c)(1),
(2) Date: Jan. 25, 2019

(87) PCT Pub. No.: WO2018/021314
PCT Pub. Date: Feb. 1, 2018

(65) Prior Publication Data
US 2019/0159943 A1     May 30, 2019

(30) Foreign Application Priority Data

Jul. 28, 2016    (JP) .............................. JP2016-148953

(51) Int. Cl.
*A61F 13/514* (2006.01)
*A61F 13/49* (2006.01)
(Continued)

(52) U.S. Cl.
CPC .... *A61F 13/5148* (2013.01); *A61F 13/49001* (2013.01); *A61F 13/4902* (2013.01);
(Continued)

(58) Field of Classification Search
CPC ............ A61F 13/5148; A61F 13/49001; A61F 13/49011; A61F 13/49017; A61F 13/511;
(Continued)

(56) References Cited

U.S. PATENT DOCUMENTS 5,882,769 A    3/1999   McCormack et al.
9,237,974 B2    1/2016   Ohashi et al.
(Continued)

FOREIGN PATENT DOCUMENTS

CN         1744870 A      3/2006
CN         1889914 A      1/2007
(Continued)

OTHER PUBLICATIONS

International Search Report, issued in PCT/JP2017/026875, PCT/ISA/210, dated Oct. 24, 2017.

*Primary Examiner* — Tatyana Zalukaeva
*Assistant Examiner* — Nhu Q. Tran
(74) *Attorney, Agent, or Firm* — Birch, Stewart, Kolasch & Birch, LLP

(57) ABSTRACT

A disposable diaper 1 has an elasticized leg cuff 10 on each longitudinally extending, lateral side of the crotch portion C. The elasticized leg cuff 10 includes an elastic member fixing sheet 5, an elastic member 6, an inner sheet 31, and an outer sheet 32 in order from the skin facing side. The inner sheet 31 and the outer sheet 32 are bonded to each other via a plurality of longitudinally extending and laterally spaced bonds 7. The elastic member 6 is located between the elastic member fixing sheet 5 and the inner sheet 31 and arranged at a location that does not overlap the bonds 7.

21 Claims, 5 Drawing Sheets

(51) Int. Cl.
*A61F 13/511* (2006.01)
*A61F 13/56* (2006.01)

(52) U.S. Cl.
CPC .. *A61F 13/49011* (2013.01); *A61F 13/49017* (2013.01); *A61F 13/49019* (2013.01); *A61F 13/511* (2013.01); *A61F 13/5622* (2013.01); *A61F 13/51401* (2013.01); *A61F 2013/49076* (2013.01)

(58) Field of Classification Search
CPC ............ A61F 13/5622; A61F 13/51401; A61F 2013/49076
USPC ........................................................ 604/385
See application file for complete search history.

(56) References Cited

U.S. PATENT DOCUMENTS

| | | | |
|---|---|---|---|
| 2004/0186453 | A1 | 9/2004 | Shimada et al. |
| 2005/0107761 | A1 | 5/2005 | Mishima et al. |
| 2005/0203479 | A1 | 9/2005 | Sakaguchi et al. |
| 2010/0076394 | A1* | 3/2010 | Hayase ............... B29C 66/1122 604/385.29 |
| 2011/0251576 | A1 | 10/2011 | Ando et al. |
| 2012/0041407 | A1* | 2/2012 | Kamiyama ........... A61F 13/496 604/385.3 |
| 2012/0095429 | A1 | 4/2012 | Kobayashi et al. |
| 2012/0330264 | A1 | 12/2012 | Lawson et al. |
| 2015/0230995 | A1* | 8/2015 | Kaneko ................. A61F 13/496 604/385.3 |
| 2016/0158072 | A1 | 6/2016 | Lawson et al. |
| 2016/0213531 | A1 | 7/2016 | Takahashi et al. |
| 2017/0319398 | A1 | 11/2017 | Lawson et al. |
| 2019/0008704 | A1 | 1/2019 | Takahashi et al. |

FOREIGN PATENT DOCUMENTS

| | | |
|---|---|---|
| CN | 1913858 A | 2/2007 |
| CN | 102245143 A | 11/2011 |
| CN | 102448418 A | 5/2012 |
| CN | 103717187 A | 4/2014 |
| CN | 104271093 A | 1/2015 |
| CN | 104837448 A | 8/2015 |
| CN | 204909840 U | 12/2015 |
| CN | 105555241 A | 5/2016 |
| JP | 2000-135240 A | 5/2000 |
| JP | 2005-245958 A | 9/2005 |
| JP | 2006-130042 A | 5/2006 |
| JP | 2007-97920 A | 4/2007 |
| JP | 2008-86505 A | 4/2008 |
| JP | 2008-284183 A | 11/2008 |
| JP | 2013-123531 A | 6/2013 |
| JP | 2016-22235 A | 2/2016 |
| RU | 2575433 C2 | 2/2016 |
| WO | WO 2014/093129 A1 | 6/2014 |

* cited by examiner

DISPOSABLE DIAPER

TECHNICAL FIELD

The present invention relates to a disposable diaper.

BACKGROUND ART

Disposable diapers having an outer nonwoven fabric sheet and a backsheet bonded together in a discontinuous pattern, such as a stripe, dot, or spiral pattern, to form an outer cover with improved touch are known, For example, Patent Literature 1 below discloses a disposable diaper having an outer laminate composed of an inner sheet and an outer sheet, the inner sheet and the outer sheet being bonded together via adhesive layers applied spacedly in a region except laterally opposite side edges of the front and the rear half.

Patent Literature 2 below discloses a disposable diaper having an outer cover composed of an outer sheet and an inner sheet, the outer cover having between the outer and the inner sheet adhesive layers applied in stripes extending in the lateral direction and spaced in the longitudinal direction of the diaper. In the elasticized region of the outer cover, a plurality of elastic members are disposed spacedly in the longitudinal direction of the diaper, and at least one of the adhesive layers is arranged between every pair of longitudinally adjacent elastic members, via which the outer sheet and the inner sheet are bonded to each other.

Patent Literature 3 discloses a disposable absorbent article having an adhesive-applied region for fixing leg elastic members. The adhesive-applied region has over the entire area thereof a plurality of rows of spirally applied adhesive layers extending in the lateral direction.

CITATION LIST

Patent Literature

Patent Literature 1: JP 2000-135240A
Patent Literature 2: JP 2016-22235A
Patent Literature 3: JP 2006-130042A

SUMMARY OF INVENTION

The invention relates to a disposable diaper comprising a topsheet on a skin facing side of the disposable diaper, a backsheet on a non-skin facing side of the disposable diaper, and an absorbent member located between the topsheet and the backsheet, and having a longitudinal direction along a wearer's front-to-back direction and a lateral direction perpendicular to the longitudinal direction. The disposable diaper has a crotch portion and an elasticized leg cuff arranged on each longitudinally extending lateral side of the crotch portion. The elasticized leg cuff includes an elastic member fixing sheet, an elastic member, an inner sheet, and an outer sheet in order from the skin facing side. The inner sheet and the outer sheet are bonded to each other via a plurality of longitudinally extending and laterally spaced bonds. The elastic member is located between the elastic member fixing sheet and the inner sheet and arranged at a location that does not overlap any of the bonds in the lateral direction.

DESCRIPTION OF EMBODIMENTS

The techniques according to Patent Literatures 1 to 3 are effective in improving the feel to the touch of the flat region (i.e., the region with no elastic member) of the crotch portion of the outer cover of disposable diapers but are still insufficient in improving the softness or touch of the elasticized region having an elastic member.

The invention relates to the provision of a disposable diaper having improved feel and appearance on its elasticized leg cuffs adapted to be worn around wearer's legs.

The invention will be described on the basis of its preferred embodiments with reference to the accompanying drawings.

Figure 1:
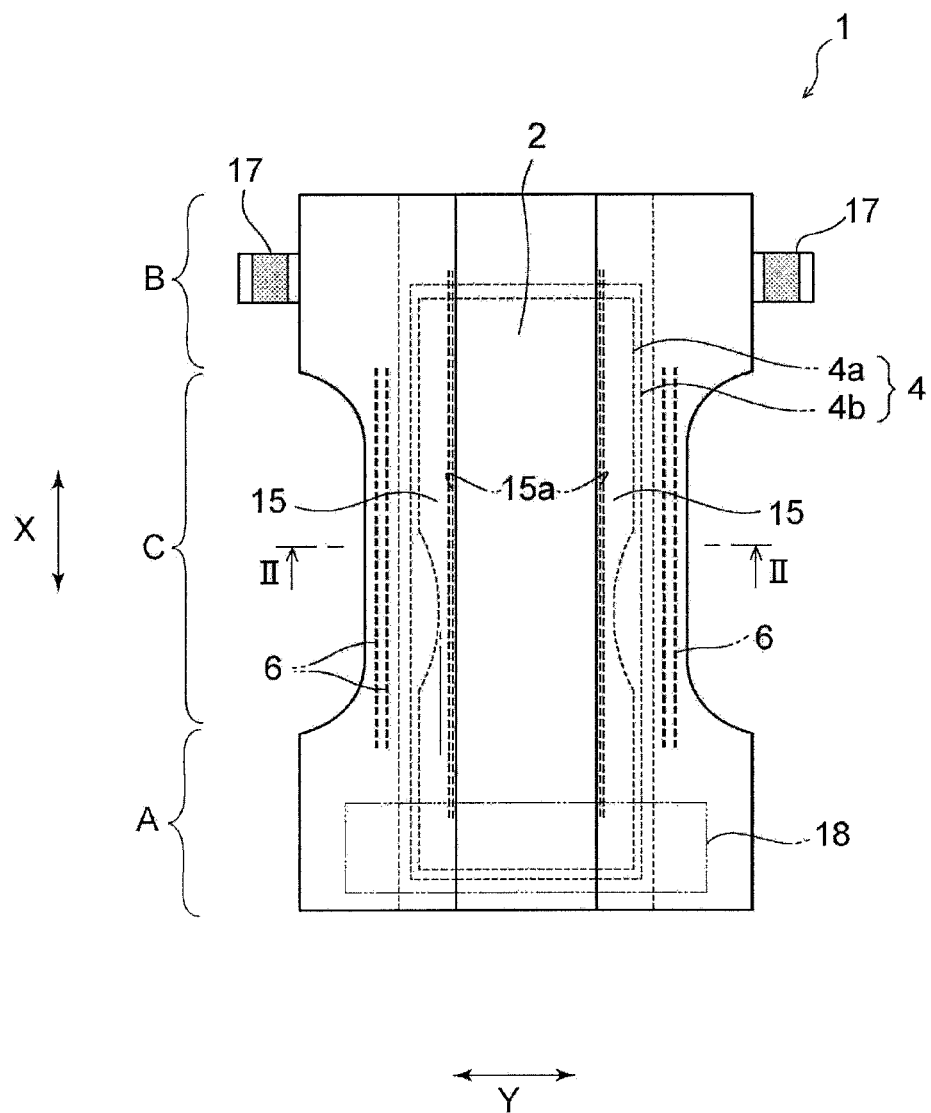
FIG. 1 is a plan view of an embodiment of the disposable diaper of the invention.

FIG. 1 illustrates a basic structure of a disposable diaper 1 (hereinafter also referred simply to "diaper 1") according to one embodiment of the invention. As illustrated, the disposable diaper 1 includes a liquid permeable topsheet 2 disposed on a skin facing side of the disposable diaper, a liquid impermeable backsheet 3 disposed on a non-skin facing side of the disposable diaper, and an absorbent member 4 interposed between the two sheets 2 and 3. As used herein, the term "skin facing side" refers to the side of the diaper 1 or a member constituting the diaper 1 (e.g., the absorbent member 4) facing the wearer's skin, i.e., the side relatively closer to the wearer's skin, while worn. The term "non-skin-facing side" refers to the side of the diaper 1 or a member constituting the diaper 1 facing away from the wearer's skin while worn, i.e., the side relatively farther from the wearer's skin, while worn. The term "liquid impermeable" as used herein with respect to the backsheet 3 includes "sparingly liquid impermeable", so that the backsheet 3 may be formed of a perfectly liquid impermeable material or a water repellent material.

The disposable diaper 1 has a longitudinal direction X along the front-to-back direction of a wearer and a lateral or transverse direction Y perpendicular to the longitudinal direction X when in a flat-out configuration as illustrated in FIG. 1. The disposable diaper 1 has a front portion A that is to be located on the front of a wearer while worn, a rear portion B that is to be located on the back of the wearer, a crotch portion C that is located intermediate between the front and the rear portion. The disposable diaper 1 is an open type disposable diaper provided with a fastening tape 17 on each lateral side edge of the rear portion B and with a landing zone 18 on the exterior surface of the front portion A to which the fastening tapes 17 are to be secured.

The absorbent member 4 in the disposable diaper 1 includes an absorbent core 4a and a core wrap sheet 4b enclosing the absorbent core 4a. The absorbent core 4a may be formed of an airlaid fiber web of absorbent fiber, such as pulp fiber, or an airlaid mixed fiber web containing the absorbent fiber and an absorbent polymer. The absorbent fiber includes cellulosic hydrophilic fibers, such as pulp fiber, rayon fiber, cotton fiber, and cellulose acetate fiber. In addition to the cellulosic hydrophilic fibers, fibers of synthetic resins, such as polyolefins, polyesters, and polyamides, having been rendered hydrophilic by a surfactant or the like are also useful. The core wrap sheet 4b may be, for example, tissue or a water permeable nonwoven fabric. The core wrap sheet 4b may be a single sheet enclosing the whole absorbent core 4a or comprise two or more sheets used in combination to enclose the core 4a. The backsheet 3 may be a liquid impermeable or water repellent resin film or a laminate of a resin film and a nonwoven fabric.

Figure 2:
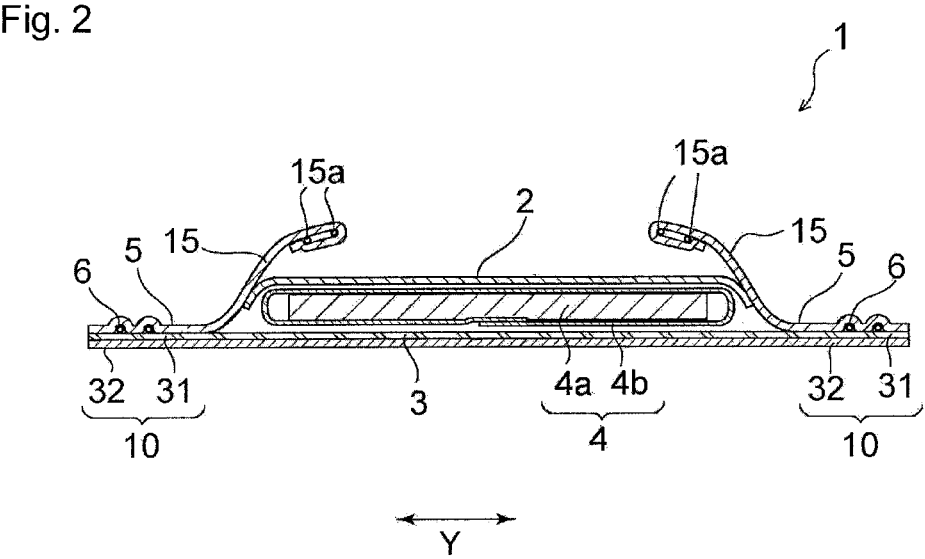
FIG. 2 is a cross-sectional view taken along line II-II of FIG. 1.

As illustrated in FIG. 2, the disposable diaper 1 has a pair of standing cuff-forming sheets 15 provided along the longitudinal direction in the crotch portion C. The standing cuff-forming sheet 15 has an elastic member 15a and, upon contraction of the elastic member 15a, rises toward the wearer's skin to form a standing cuff in the crotch portion C while worn.

The disposable diaper 1 has an elasticized leg cuff 10 arranged on each longitudinally extending, lateral side portion of the crotch portion C. Specifically, the elasticized leg cuff 10 is provided on each lateral side portion extending laterally outward of each longitudinally extending side edge of the absorbent member 4.

The elasticized leg cuff 10 has an elastic member fixing sheet 5, an elastic member 6, an inner sheet 31, and an outer sheet 32 in order from the skin facing side as illustrated in FIG. 2.

Figure 3A:
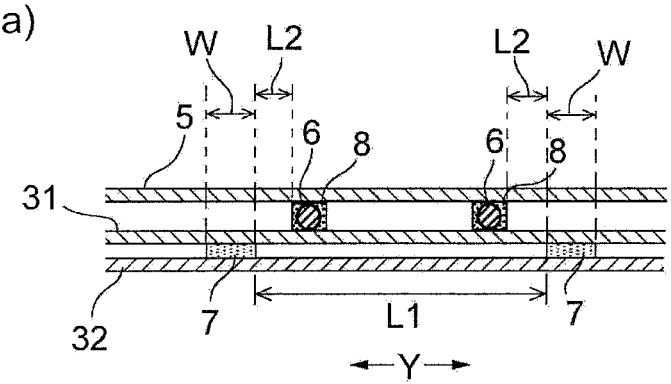
FIG. 3(a), FIG. 3(b), and FIG. 3(c) are each a schematic cross-sectional view showing a preferred structure of the elasticized leg cuff of the disposable diaper of FIG. 1, taken along the lateral direction (along line II-II of FIG. 1).
Figure 3B:
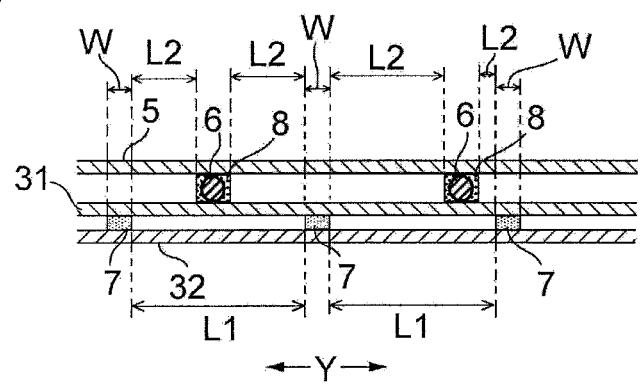
Figure 3C:
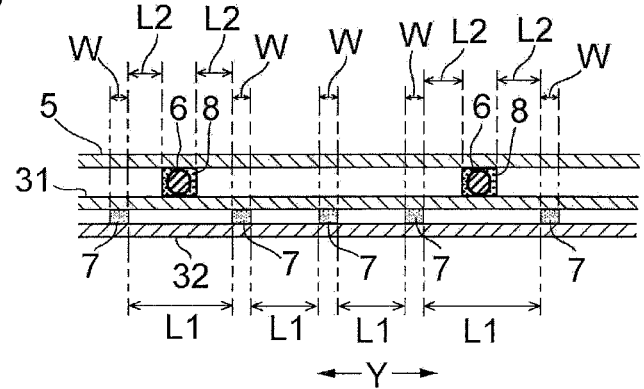

The inner sheet 31 and the outer sheet 32 in the elasticized leg cuff 10 are bonded to each other at a plurality of bonds 7 extending in the longitudinal direction X and spaced in the lateral direction Y. As illustrated in FIGS. 3(a), 3(b), and 3(c), the adjacent bonds 7 are discrete from each other, namely, spacedly arranged in the lateral direction Y.

The bonds 7 can be formed by various means, such as adhesive bonding or fusion bonding. The adhesive may be of any type commonly used in absorbent articles such as disposable diapers, such as hot melt adhesives. Useful hot melt adhesives include block copolymer hot melt adhesives, such as styrene-isoprene-styrene block copolymers (SIS), styrene-butadiene-styrene block copolymers (SBS), and styrene-ethylene-butylene-styrene copolymers (SEBS). Any fusion bonding techniques conventionally used in absorbent articles such as disposable diapers, including heat sealing, high-frequency sealing, and ultrasonic sealing, may be used. Heat, ultrasonic, or high-frequency fusion bonding can be used to form the bonds 7 when the inner sheet 31 and the outer sheet 32 are formed of fusible materials.

The elastic member 6 is disposed between the elastic member fixing sheet 5 and the inner sheet 31. The elastic member 6 is arranged between laterally adjacent bonds 7 at a location that does not overlap the bonds 7 in plan view. The elastic member 6 is fixed in a stretched condition between the elastic member fixing sheet 5 and the inner sheet 31 along the longitudinal direction X so that, the elasticized leg cuff 10 forms leg gathers due to contraction of the elastic member 6 while the diaper 1 is worn. The elastic member 6 may be fixed by, for example, sandwiching the elastic member 6 having adhesive 8 previously applied thereto between the elastic member fixing sheet 5 and the inner sheet 31 or by applying adhesive to the elastic member fixing sheet 5 or the inner sheet 31 and sandwiching the elastic member 6 therebetween. In the present embodiment, the former method for fixing the elastic member 6 is preferred. In the former method, adhesive 8 is preferably applied to a whole circumference of the elastic member 6.

The elastic member 6 is arranged so as not to overlap any bonds 7 in the lateral direction Y (in plan view). FIGS. 3(a) to 3(c), which are cross-sections in the thickness direction of the elasticized leg cuff 10, show examples of the arrangement of the bonds 7 and the elastic members 6 in the lateral direction Y. In every example of the arrangement, the elastic member 6 does not overlap the bond 7 in the lateral direction Y. To achieve such an arrangement, the bonds 7 are preferably formed by applying adhesive in a stripe pattern using a coater. With the adhesive applied in a stripe pattern, it is easy to locate the bonds 7 so as not to overlap the elastic member 6 in the lateral direction Y as compared with when adhesive is applied in a spiral pattern.

In the case where the two elasticized leg cuffs 10, one on each side of the crotch portion C, each contain a plurality of elastic members 6, it is only necessary that at least one of the plurality of elastic members 6 per side be located not to overlap any of adjacent bonds 7 in the lateral direction Y. Preferably, part of the plurality of elastic members 6, more preferably all the elastic members 6 are located not to overlap any of adjacent bonds 7 in the lateral direction Y.

Figure 4A:
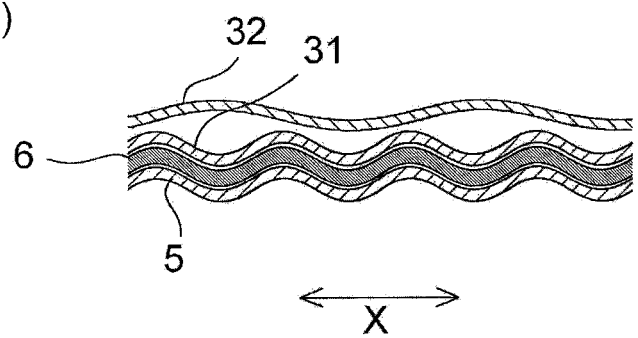
FIG. 4(a) is a schematic cross-sectional view of the elasticized leg cuff of the disposable diaper of FIG. 1, taken in the longitudinal direction.

While the elastic member 6 is fixed in its stretched condition along the longitudinal direction X between the elastic member fixing sheet 5 and the inner sheet 31 as illustrated in FIG. 1, it contracts to deform into a wavy condition while in use. Since the elastic member 6 and the bonds 7 are arranged at the above described locations, the outer sheet 32 is restrained from following the deformation of the elastic member 6. In other words, because of the absence of bonds 7 at the location of the elastic member 6 in the lateral direction Y, the space formed between the inner sheet 31 and the outer sheet 32 restrains the outer sheet 32 from being deformed into a finely wavy condition with the deformation of the elastic member 6, thereby confining the deformation of the outer sheet 32 to a gently wavy condition as illustrated in FIG. 4(a). As a result, the outer side (the side of the outer sheet 32) of each elasticized leg cuff 10 of the diaper 1 feels soft when touched by the wearer, parent, or caregiver. The elasticized leg cuffs 10 also visually give the wearer, parent, or caregiver a feeling of softness and reassure the wearer, parent, or caregiver about the kindness to the skin. Furthermore, the appearance of the elasticized leg cuffs 10 reassures the wearer, parent, or caregiver that the diaper is not too constrictive around the legs and leaves no pressure marks.

Figure 4B:
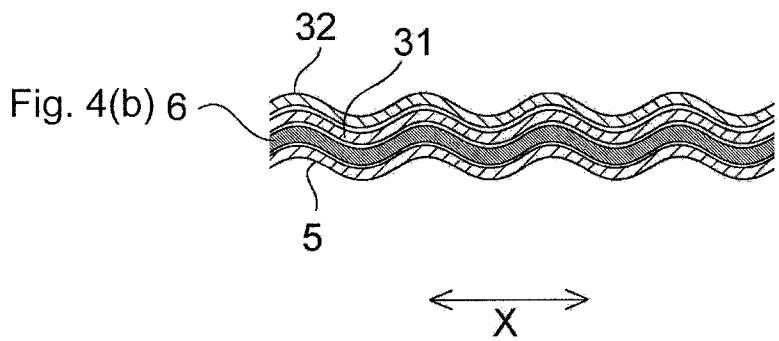
FIG. 4(b) is a schematic cross-sectional view of an elasticized leg cuff of a conventional disposable diaper, taken in the longitudinal direction.

In contrast, if the elastic member 6 is located to overlap the bond 7 in the lateral direction Y, the outer sheet 32 will be deformed following the deformation of the elastic member 6 as illustrated in FIG. 4(b), and the thus deformed elasticized leg cuffs 10 can visually give a feeling of hardness.

In the embodiment shown in FIGS. 3(a) to 3(c) the elastic members 6 are each located between two adjacent bonds 7 in the lateral direction Y. Because of the presence of the bond 7 on both lateral sides of each elastic member 6, the sheets composing the elasticized leg cuff 10 are prevented from sliding relative to each other while securing the softness of the outer sheet 32.

In the embodiment, the inner sheet 31 is the backsheet 3 that extends laterally outward from each lateral side edge of the absorbent member 4. Although the backsheet 3, being formed of a resin film, a laminate of a resin film and a nonwoven fabric, or the like, tends to have a hard feel to the touch, the provision of the outer sheet 32 on the non-skin facing side of the back sheet 3 in the above described fashion can bring about practical and visual softness of the outer sheet 32 while securing protection by the backsheet 3 against leakage. While it is preferred that the elastic member 6 be located between two adjacent bonds 7 with no overlap with the bonds 7 in the lateral direction Y, the elastic member 6 may be located laterally outside two adjacent bonds 7.

The distance L1 between adjacent bonds 7 in the lateral direction Y is preferably 0.5 mm or greater, more preferably 0.7 mm or greater, even more preferably 1.0 mm or greater, preferably 10.0 mm or smaller, more preferably 7.0 mm or smaller, even more preferably 5.0 mm or smaller, and preferably 0.5 to 10.0 mm, more preferably 0.7 to 7.0 mm, even more preferably 1.0 to 5.0 mm. With the distance L1 being in the above preferred ranges, the outer sheet is allowed to wave to a moderate degree such that the outer sheet and the inner sheet may not slide relative to each other. The distance L1 is the shortest distance between two adjacent bonds 7 in the lateral direction Y as indicated in FIGS. 3(a) to 3(c). In the case where more than two bonds 7 are laterally spacedly disposed in each elasticized leg cuff 10, it is preferred that at least one of the spaces between adjacent bonds 7 be in the above range, and it is more preferred that every space between adjacent bonds 7 be in the above range. It is also preferred that one or more pairs of adjacent bonds 7 having the elastic member 6 between them in the lateral direction Y have a distance L1 falling in the above range. The distances L1 between different pairs of adjacent bonds 7 may be the same or different.

The distance L2 between the elastic member 6 and the adjacent bond 7 in the lateral direction Y is preferably 0.5 mm or greater, more preferably 0.7 mm or greater, even more preferably 1.0 mm or greater, preferably 10.0 mm or smaller, more preferably 7.0 mm or smaller, even more preferably 5.0 mm or smaller, and preferably 0.5 to 10.0 mm, more preferably 0.7 to 7.0 mm, even more preferably 1.0 to 5.0 mm. With the distance L2 being in that range, the disposable diaper 1 assumes an appearance such that the contraction of the elastic member 6 is unnoticeable to the wearer, parent, or caregiver. That is, since the wavy deformation of the outer sheet 32 is gentle, the outer sheet 32 appears to be soft (fluffy). The distance L2 is the shortest distance from one side of the elastic member 6 to the nearest bond 7 in the lateral direction Y as illustrated in FIGS. 3(a) to 3(c). When the elastic member 6 is located between two adjacent bonds 7, it is preferred that the distances L2 on both sides of the elastic member 6 be each in the above range. When the elastic member 6 is located between two adjacent bonds 7, the distances L2 on both sides of the elastic member 6 may be the same or different.

When there are more than one pairs of adjacent bonds 7 having the elastic member 6 between them in the lateral direction Y, it is preferred that the distances L2 on both sides of at least one elastic member 6 be in the above range, and it is more preferred that the distances L2 on both sides of every elastic member 6 be in the above range.

The width W of the bond 7 in the lateral direction Y is preferably 0.5 mm or larger, more preferably 0.7 mm or larger, even more preferably 1.0 mm or larger, preferably 5.0 mm or smaller, more preferably 3.0 mm or smaller, even more preferably 2.0 mm or smaller, and preferably 0.5 to 5.0 mm, more preferably 0.7 to 3.0 mm, even more preferably 1.0 to 2.0 mm. With the width W being in that range, it is easy to secure the adhesive strength between the outer sheet 32 and the inner sheet 31 while maintaining the softness of the elasticized leg cuff 10. The widths W of the plurality of bonds 7 may be the same or different.

It is preferable in the embodiment that the elasticized leg cuff 10 have two or more elastic members 6 and that two adjacent elastic members 6 have at least one of the bonds 7 therebetween. For example, one bond 7 is provided between adjacent elastic members 6 in the lateral direction Y as in the case of FIG. 3(b), or three bonds 7 are provided between adjacent elastic members 6 as in the case of FIG. 3(c). Such an arrangement is more effective in developing softness (a fluffy feel) of the elasticized leg cuff 10.

Being of an open type, the disposable diaper 1 of the embodiment preferably has opposed lateral side edges of the crotch portion C concaved inwardly in the lateral direction Y. So configured, the diaper 1 is capable of enclosing the wearer's lower torso without exposing the buttocks and effective in preventing an excessive constrictive force from being applied.

The term "concaved inwardly" as used herein with respect to the shape of the crotch portion means not only being curved in over the entire edge of the crotch portion C, i.e., from the end of the rear portion B to the end of the front portion A, but also being curved in but containing a longitudinally straight portion in the longitudinally central part of the crotch portion C.

Figure 5:
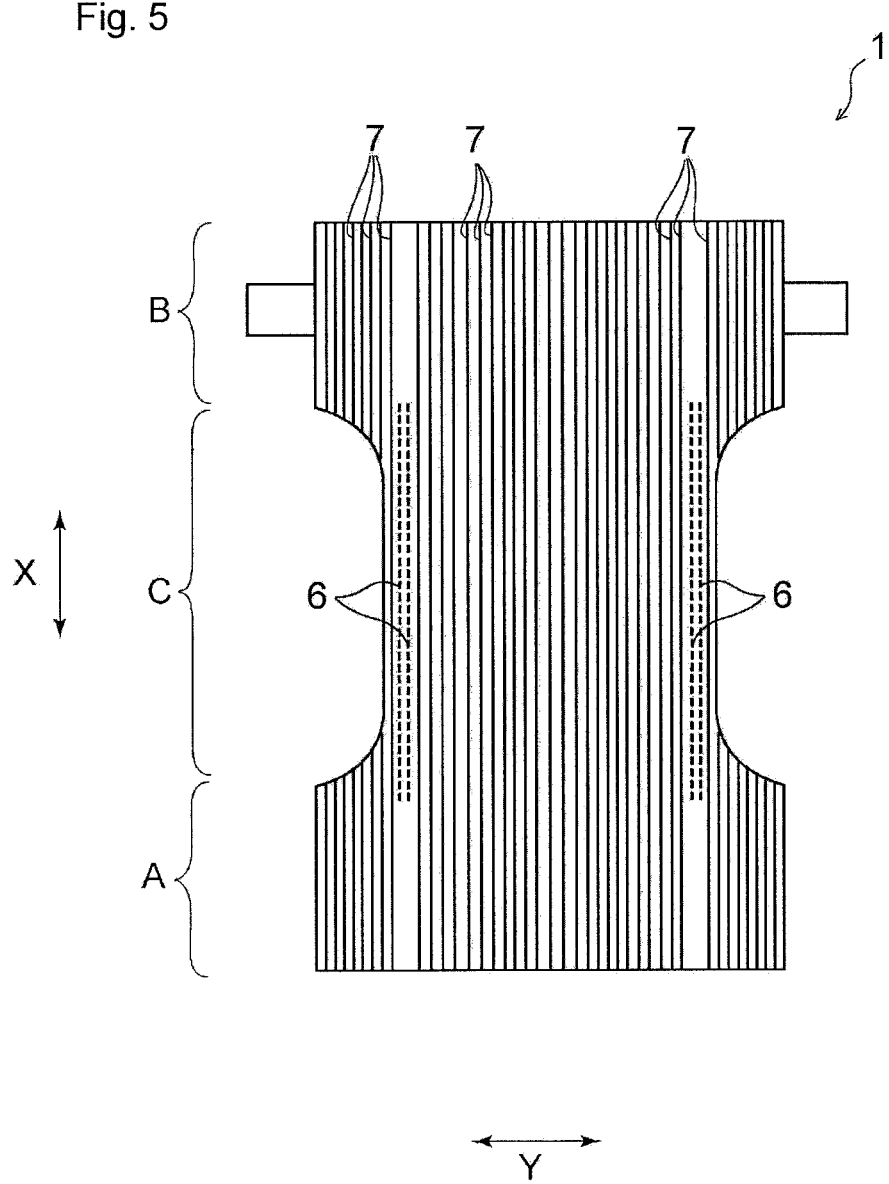
FIG. 5 is a schematic plan view illustrating the pattern of bonding the outer sheet and the inner sheet in the disposable diaper of FIG. 1.

In the embodiment, as illustrated in FIG. 5, the crotch portion C has the inner sheet 31 and the outer sheet 32 over the entire width thereof in the lateral direction Y, and the inner sheet 31 and the outer sheet 32 are bonded to each other even in the region overlapping the absorbent member 4 via a plurality of longitudinally extending and laterally spaced bonds (second bonds). So configured, the diaper feels fluffier as a whole, which is expected to remind the user of the softness of the portions worn around the legs. Unlike the bonds 7 in the elasticized leg cuffs 10, the second bonds may be arranged regardless of overlap with the elastic members 6 in the lateral direction Y. That is, the second bonds may or may not overlap the elastic member 6 in the lateral direction Y.

Materials of the elastic member 6 include synthetic rubbers, such as styrene-butadiene rubber, butadiene rubber, isoprene rubber, and neoprene rubber; natural rubber, EVA, stretch polyolefins, and polyurethanes. The elastic member 6 may have the form of a yarn with a rectangular, square, circular, elliptic, polygonal, or a like cross-sectional shape (e.g., rubber yarn) or the form of a cord (e.g., rubber string), or a multifilamentous elastic yarn. A rubber yarn is preferred.

The width of the elastic member 6 in the lateral direction Y is preferably 0.1 mm or greater with a view to elasticize the leg cuff portion and preferably 0.3 mm or smaller with a view to facilitate the arrangement of the elastic member 6 with no overlap with the bonds 7 in the lateral direction Y. The width is more preferably 0.1 to 0.3 mm. When the elastic member 6 is a rubber yarn, the width of the elastic member 6 in the lateral direction Y corresponds to the diameter of the rubber yarn.

The outer sheet is preferably a nonwoven fabric in view of touch and visual softness. Nonwoven fabrics produced by various methods may be used with no particular limitation, including air-through, spun-bonded, melt-blown, and hydroentangled nonwoven fabrics.

The elastic member 6 may be fixed between the outer sheet 32 and the inner sheet 31 by applying adhesive, such as a hot melt adhesive, to either the outer sheet 32 or the inner sheet 31, disposing the elastic member 6 on the applied adhesive, and superposing the other sheet under pressure or applying adhesive, such as a hot melt adhesive, directly to the elastic member 6 using, for example, a comb gun, and fixing the elastic member 6 to one or both of the outer sheet 32 and the inner sheet 31 via the adhesive. The latter method is preferred.

In consideration of the above embodiments of the present invention, the following disposable diaper are further disclosed.

<1> A disposable diaper comprising a topsheet on a skin facing side of the disposable diaper, a backsheet on a non-skin facing side of the disposable diaper, and an absorbent member located between the topsheet and the backsheet, and having a longitudinal direction along a wearer's front-to-back direction and a lateral direction perpendicular to the longitudinal direction, the disposable diaper having a crotch portion and an elasticized leg cuff arranged on each longitudinally extending lateral side of the crotch portion, the elasticized leg cuff comprising an elastic member fixing sheet, an elastic member, an inner sheet, and an outer sheet in order from the skin facing side, the inner sheet and the outer sheet being bonded to each other via a plurality of longitudinally extending and laterally spaced bonds, and the elastic member being located between the elastic member fixing sheet and the inner sheet and arranged at a location that does not overlap any of the bonds in the lateral direction.

<2> The disposable diaper as set forth in clause <1>, wherein the elastic member has the form of a yarn.

<3> The disposable diaper as set forth in clause <2>, wherein the elastic member has a rectangular, square, circular, elliptic, or polygonal cross-sectional shape.

<4> The disposable diaper as set forth in any one of clauses <1> to <3>, wherein the elastic member has a width of preferably 0.1 mm or greater, preferably 0.3 mm or smaller more preferably 0.1 to 0.3 mm measured in the lateral direction.

<5> The disposable diaper as set forth in any one of clauses <1> to <4>, wherein the bonds are formed of adhesive, preferably hot melt adhesives.

<6> The disposable diaper as set forth in any one of clauses <1> to <5>, wherein the elastic member is fixed in a longitudinally stretched condition between the elastic member fixing sheet and the inner sheet.

<7> The disposable diaper as set forth in any one of clauses <1> to <6>, wherein the elastic member is fixed between the elastic member fixing sheet and the inner sheet by applying adhesive to a whole circumference of the elastic member and then sandwiching the elastic member between the elastic member fixing sheet and the inner sheet.

<8> The disposable diaper as set forth in any one of clauses <1> to <7>, wherein the bonds are formed by applying adhesive in a stripe pattern.

<9> The disposable diaper as set forth in any one of clauses <1> to <8>, wherein the elastic member is located between two adjacent bonds in the lateral direction.

<10> The disposable diaper as set forth in any one of clauses <1> to <9>, wherein the disposable diaper has the elastic member located laterally outside two adjacent bonds.

<11> The disposable diaper as set forth in any one of clauses <1> to <10>, wherein the inner sheet is the backsheet extending from each lateral side edge of the absorbent member.

<12> The disposable diaper as set forth in any one of clauses <1> to <11>, wherein the distance L1 between adjacent bonds is preferably 0.5 mm or greater, more preferably 0.7 mm or greater, even more preferably 1.0 mm or greater, and preferably 10.0 mm or smaller, more preferably 7.0 mm or smaller, even more preferably 5.0 mm or smaller in the lateral direction.

<13> The disposable diaper as set forth in any one of clauses <1> to <12>, wherein the distance L1 between adjacent bonds is 0.5 to 10.0 mm in the lateral direction.

<14> The disposable diaper as set forth in any one of clauses <1> to <13>, wherein the distance L2 between the elastic member and its adjacent bond is preferably 0.5 mm or greater, more preferably 0.7 mm or greater, even more preferably 1.0 mm or greater, and preferably 10.0 mm or smaller, more preferably 7.0 mm or smaller, even more preferably 5.0 mm or smaller in the lateral direction.

<15> The disposable diaper as set forth in any one of clauses <1> to <14>, wherein the distance L2 between the elastic member and its adjacent bond is 0.5 to 10.0 mm in the lateral direction.

<16> The disposable diaper as set forth in any one of clauses <1> to <15>, wherein the elastic member is located between two adjacent bonds, and the distance L2 on both sides of the elastic member is each preferably 0.5 mm or greater, more preferably 0.7 mm or greater, even more preferably 1.0 mm or greater, and preferably 10.0 mm or smaller, more preferably 7.0 mm or smaller, even more preferably 5.0 mm or smaller in the lateral direction.

<17> The disposable diaper as set forth in any one of clauses <1> to <16>, wherein the bonds each have a width W of preferably 0.5 mm or larger, more preferably 0.7 mm or larger, even more preferably 1.0 mm or larger, and preferably 5.0 mm or smaller, more preferably 3.0 mm or smaller, even more preferably 2.0 mm or smaller in the lateral direction.

<18> The disposable diaper as set forth in any one of clauses <1> to <17>, wherein the bonds each have a width W of 0.5 to 5.0 mm in the lateral direction.

<19> The disposable diaper as set forth in any one of clauses <1> to <18>, wherein the elasticized leg cuff has two or more elastic members, and two adjacent elastic members have at least one of the bonds therebetween.

<20> The disposable diaper as set forth in any one of clauses <1> to <19>, being of an open type and having opposed lateral side edges of the crotch portion concaved inwardly in the lateral direction.

<21> The disposable diaper as set forth in any one of clauses <1> to <20>, wherein the crotch portion has the inner sheet and the outer sheet over the entire width thereof in the lateral direction, and the inner sheet and the outer sheet are bonded to each other even in the region overlapping the absorbent member via a plurality of longitudinally extending and laterally spaced bonds.

INDUSTRIAL APPLICABILITY

The invention provides a disposable diaper having an improved feel to the touch and an improved appearance on its elasticized leg cuffs provided in portions adapted to be worn around the legs of a wearer.

The invention claimed is:

1. A disposable diaper comprising a topsheet on a skin facing side of the disposable diaper, a backsheet on a non-skin facing side of the disposable diaper, and an absorbent member located between the topsheet and the backsheet, and having a longitudinal direction along a wearer's front-to-back direction and a lateral direction perpendicular to the longitudinal direction, the disposable diaper having a crotch portion and an elasticized leg cuff arranged on each longitudinally extending lateral side of the crotch portion, the elasticized leg cuff comprising an elastic member fixing sheet, an elastic member, an inner sheet, and an outer sheet in order from the skin facing side, the inner sheet and the outer sheet being bonded to each other via a plurality of longitudinally extending and laterally spaced bonds in a continuous stripe pattern, and in the elasticized leg cuff, the inner sheet and the outer sheet being not bonded at an area other than the bonds, the elastic member being located between the elastic member fixing sheet and the inner sheet and arranged at a location that does not overlap any of the bonds in the lateral direction, and thereby (i) restraining the outer sheet from being deformed into a finely wavy condition caused by deformation of the elastic member and (ii) allowing the outer sheet to possess a gentle wavy visual appearance.

2. The disposable diaper according to claim 1, wherein the elastic member has the form of yarn.

3. The disposable diaper according to claim 2, wherein the elastic member has a rectangular, square, circular, elliptic, or polygonal cross-sectional shape.

4. The disposable diaper according to claim 1, wherein the elastic member has a width of 0.1 to 0.3 mm measured in the lateral direction.

5. The disposable diaper according to claim 1, wherein the bonds are formed of adhesive.

6. The disposable diaper according to claim 1, wherein the elastic member is fixed in a longitudinally stretched condition between the elastic member fixing sheet and the inner sheet.

7. The disposable diaper according to claim 1, wherein the elastic member is fixed between the elastic member fixing sheet and the inner sheet by applying adhesive to a whole circumference of the elastic member and then sandwiching the elastic member between the elastic member fixing sheet and the inner sheet.

8. The disposable diaper according to claim 1, wherein the bonds are formed by applying adhesive in a stripe pattern.

9. The disposable diaper according to claim 1, wherein the elastic member is located between two adjacent bonds in the lateral direction.

10. The disposable diaper according to claim 1, wherein the disposable diaper has the elastic member located laterally outside two adjacent bonds.

11. The disposable diaper according to claim 1, wherein the inner sheet is the backsheet extending from each lateral side edge of the absorbent member.

12. The disposable diaper according to claim 1, wherein a distance (L1) between adjacent bonds is 0.5 to 10.0 mm in the lateral direction.

13. The disposable diaper according to claim 1, wherein a distance (L1) between adjacent bonds is 0.7 to 7.0 mm in the lateral direction.

14. The disposable diaper according to claim 1, wherein a distance (L2) between the elastic member and its adjacent bond is 0.5 to 10.0 mm in the lateral direction.

15. The disposable diaper according to claim 1, wherein a distance (L2) between the elastic member and its adjacent bond is 0.7 to 7.0 mm in the lateral direction.

16. The disposable diaper according to claim 1, wherein the elastic member is located between two adjacent bonds, and a distance (L2) on both sides of the elastic member is each 0.5 to 10.0 mm in the lateral direction.

17. The disposable diaper according to claim 1, wherein the bonds each have a width (W) of 0.5 to 5.0 mm in the lateral direction.

18. The disposable diaper according to claim 1, wherein the elasticized leg cuff has two or more elastic members, and two adjacent elastic members have at least one of the bonds therebetween.

19. The disposable diaper according to claim 1, having opposed lateral side edges of the crotch portion concaved inwardly in the lateral direction.

20. The disposable diaper according to claim 1, wherein the crotch portion has the inner sheet and the outer sheet over the entire width thereof in the lateral direction, and the inner sheet and the outer sheet are bonded to each other even in the region overlapping the absorbent member via a second plurality of longitudinally extending and laterally spaced bonds.

21. The disposable diaper according to claim 1, wherein said diaper further comprises a pair of fastening tapes.

\* \* \* \* \*